United States Patent [19]

Stein et al.

[11] Patent Number: 5,501,850
[45] Date of Patent: Mar. 26, 1996

[54] USE OF BENZIMIDAZOLE DERIVATIVES AS LIGHT PROTECTION FILTERS

[75] Inventors: Ingeborg Stein, Erzhausen; Ulrich Heywang, Darmstadt; Alexander Putz, Michelstadt; Roland Martin, Weinheim, all of Germany

[73] Assignee: Merck Patent Gesellschaft Mit Beschrankter Haftung, Darmstadt, Germany

[21] Appl. No.: 133,071

[22] PCT Filed: Feb. 2, 1993

[86] PCT No.: PCT/EP93/00233

§ 371 Date: Oct. 13, 1993

§ 102(e) Date: Oct. 13, 1993

[87] PCT Pub. No.: WO93/15712

PCT Pub. Date: Aug. 19, 1993

[30] Foreign Application Priority Data

Feb. 13, 1992 [DE] Germany ............... 42 04 257.7

[51] Int. Cl.[6] .................. A61K 31/415; A61K 7/42; C07D 235/18

[52] U.S. Cl. ............... 424/59; 424/60; 514/385; 548/301.7

[58] Field of Search ............ 424/59, 60; 514/385; 548/301.7

[56] References Cited

U.S. PATENT DOCUMENTS 3,095,422  6/1963  Duennenberger et al. ............. 548/224
4,775,526  10/1988  Lang et al. ............................ 424/59 X

*Primary Examiner*—Shean C. Wu
*Attorney, Agent, or Firm*—Millen, White, Zelano & Branigan

[57] ABSTRACT

The invention relates to the use of benzimidazole derivatives of the formula I,

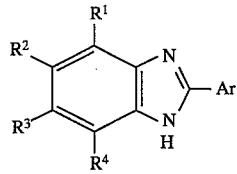

where $R^1$, $R^2$, $R^3$, $R^4$ and Ar have the meaning given in claim 1, as light protection filters in cosmetic formulations, at least one of the radicals $R^1$ to $R^4$ or an alkyl or alkoxy substituent of the group Ar containing at least 4 C atoms.

11 Claims, No Drawings

USE OF BENZIMIDAZOLE DERIVATIVES AS LIGHT PROTECTION FILTERS

The invention relates to the use of benzimidazole derivatives of the formula I

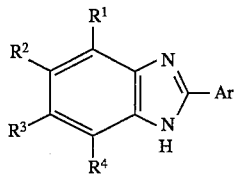

in which

R$^1$, R$^2$, R$^3$ and R$^4$ in each case independently of one another are H, alkyl or alkoxy having 1 to 10 C atoms and Ar is phenyl which is unsubstituted or substituted by 1–5 aminoalkyl, alkyl, (cyclo)alkoxy, hydroxyl or hydroxyalkoxy groups having 1 to 10 C atoms or benzimidazole-2-yl-phenyl which is monosubstituted by 1 to 2 alkyl groups having 1 to 10 C atoms, as light protection filters in cosmetic formulations, at least one of the radicals R$^1$ to R$^4$ or an alkyl or alkoxy substituent of the group Ar having at least 4 C atoms.

BACKGROUND OF THE INVENTION

As is known, the skin reacts sensitively to the sun's rays, which can cause common sunburn or erythema, and also more or less severe burns.

However, the sun's rays also have other adverse effects: they cause the skin to lose its elasticity and develop wrinkles and thus lead to premature ageing. Dermatoses can also sometimes be observed. In the extreme case, skin cancer occurs in some people.

It is also desirable to protect hair from photochemical damage, in order to prevent changes in color shades, bleaching or damage of a mechanical nature.

It is known that the components contained in cosmetic preparations are not always sufficiently stable to light and decompose under the action of light rays.

As is known, ultraviolet rays with a wavelength of less than 400 nm form the most dangerous part of the sun's rays. It is also known that because of the presence of the ozone layer of the earth's atmosphere, which absorbs some of the solar radiation, the lower limit of the ultraviolet rays which reach the earth's surface is about 280 nm.

It thus appears desirable to provide compounds which can absorb UV rays in a wavelength range of 280 to 400 nm, that is to say also UV-B rays with a wavelength of between 280 and 320 nm, which play a decisive role in the development of a solar erythema, and also UV-A rays with a wavelength between 320 and 400 nm, which tan the skin but also age it, promote initiation of an erythematous reaction or intensify this reaction in certain people or can even induce phototoxic or photoallergic reactions.

The sunscreen filters nowadays customary in cosmetics are classified into UVA and UVB filters. While there are good filters in the UVB range (280–320 nm) with substances such as EUSOLEX® 6300 or EUSOLEX® 232, those used in the UVA range (320–400 nm) present problems:

Dibenzoylmethanes, such as PARSOL® 1789 or EUSOLEX® 8020, do not have an unlimited stability when exposed to UV irradiation, which on the one hand reduces the effectiveness of the filter in the course of time and on the other hand can promote photosensitizations of the skin in isolated cases. The benzophenones also used as UVA filters have only a limited solubility in the oils used in cosmetics, and they have a relatively low absorption. On the other hand, only a few water-soluble UVA filters are currently known, but their UV absorption is low.

It is known from German Reichspatent No. 676/03 that similar benzimidazole derivatives can be used as radiation protection agents, but the compounds described therein merely contain methyl or methoxy substituents. Some of those to be used according to the invention as light protection filters are known (for example DE-A 35 33 308) and some are new.

SUMMARY OF THE INVENTION

It has been found that 2-phenylbenzimidazole derivatives which have at least one butyl or butyloxy or higher or alkoxy group, in particular a 2-ethylhexyloxy group, have outstanding UVB or UVA-B filter properties. Their solubility in the oils used in cosmetics, in particular paraffin oil, neutral oil or isopropyl myristate, is very good, so that use concentrations of up to at least 10% of the formulation are possible, even in complicated formulations.

If the extinction in the UVA range has a minimum, this is not a disadvantage, since a UVA filter can be co-incorporated into the formulation without problems.

In addition to their good properties as filters, the compounds according to the invention are distinguished by a good thermal and photochemical stability.

These compounds furthermore offer the advantage of not being toxic or irritating and of being completely harmless to the skin.

They are distributed uniformly in the conventional cosmetic carriers, and can form a continuous film, in particular in fat carriers. Further, they can be applied to the skin in this manner, in order to form an effective protective film.

The invention relates to the use of the compounds of the abovementioned formula I as light protection filters in cosmetic formulations.

A preferred embodiment is the use of benzimidazoles of the formula Ia,

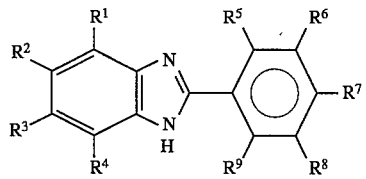

wherein at least one of the groups R$^1$ to R$^9$ is alkyl or alkoxy having 4 to 10 C atoms and the other groups R$^1$ to R$^9$ are H, alkyl or alkoxy having 1 to 10 C atoms, as light protection agents in cosmetic formulations.

The invention furthermore relates to the new benzimidazoles of the formula Ia wherein at least one of the groups R$^1$ to R$^9$ is a 2-ethylhexyloxy group and the other groups R$^1$ to R$^9$ are H, alkyl or alkoxy having 1 to 10 C atoms.

The invention furthermore relates to cosmetic formulations which comprise, as a light protection filter, an active amount of at least one compound of the formula I, preferably of the formula Ia, in particular wherein at least one of the radicals R$^1$ to R$^9$ is 2-ethylhexyloxy, in a cosmetically compatible carrier, in particular cosmetic formulations which comprise 0.5 to 10% by weight of at least one compound of the formula I.

The invention furthermore relates to cosmetic formulations which additionally comprise a UV-B filter or UV-A filter.

Of the new compounds of the formula Ia wherein at least one of the radicals $R^1$ to $R^9$ is 2-ethylhexyloxy, those of the formula Ia1 are particularly preferred:

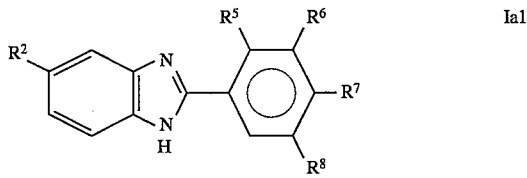

wherein $R^2$ is H or alkyl having 1 to 6 C atoms, one or two of the radicals $R^5$ to $R^8$ is/are 2-ethylhexyloxy and the others are H or methoxy.

In the compounds of the formulae I and Ia, $R^1$ to $R^4$ are H, alkyl or alkoxy having 1 to 10 C atoms, preferably H or unbranched alkyl or alkoxy groups having 1 to 8, in particular having 1 to 6 C atoms, or a branched alkyl or alkoxy group having 3 to 8, in particular having 4 to 8 C atoms, the 2-ethylhexyloxy group being particularly preferred.

Preferably, three of the radicals $R^1$ to $R^4$, preferably $R^1$, $R^3$ and $R^4$, are H and one, preferably $R^2$, is H or n-alkyl having 1 to 6 C atoms, in particular methyl.

Preferred compounds of the formula Ia are those of the formulae Ia2 and Ia3.

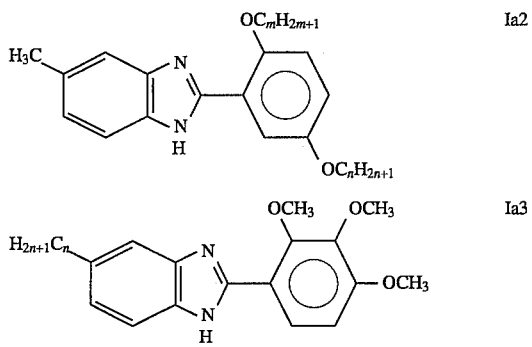

wherein m and n in each case independently of one another are an integer from 4 to 10, preferably from 6 to 8.

The compounds of the formula I are prepared by processes analogous to known processes (for example according to DE-A 35 33 308 or P. N. Preston, Chemical Reviews Volume 74, No. 3 (1974), (pages 279–311), but in particular by reaction of the corresponding arylaldehydes of the formula

Ar—CHO with the corresponding o-phenylenediamines of the formula

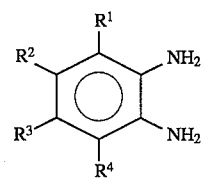

in the presence of, for example, copper(II) acetate or sodium disulfite.

1st Process

The o-phenylenediamine is preferably added to the copper(II) compound in a protic solvent, in particular an alcohol, such as, for example, methanol, ethanol or isopropanol, or water or a mixture of these solvents mentioned. The arylaldehyde is as a rule added to this mixture in a protic solvent and the mixture is preferably heated to the boiling point of the solvent.

2nd Process

The corresponding arylaldehyde is preferably reacted with sodium bisulfite in a protic solvent. The corresponding o-phenylenediamine is added to the bisulfite adduct formed by this reaction.

After heating, preferably to the boiling point of the solvent, the mixture is worked up in the customary manner.

The cosmetic agent according to the invention can be used as an agent for protecting the human epidermis or the hair or as a sunscreen agent.

The invention furthermore relates to a process for protecting the skin and natural or sensitized hair from the sun's rays, an active amount of at least one compound of the formula I, preferably of the formula Ia, in particular wherein at least one of the radicals $R^1$ to $R^9$ is 2-ethylhexyloxy, being applied to the skin or hair.

"Sensitized hair" means hair which has been subjected to a permanent wave treatment or a dyeing or bleaching process.

The invention furthermore relates to a colored or non-colored light-stabilized cosmetic formulation which comprises an active amount of at least one benzimidazole derivative of the above formula I, preferably of the formula Ia, in particular wherein at least one of the radicals $R^1$ to $R^9$ is 2-ethylhexyloxy.

If the cosmetic agent according to the invention is used as an agent for protecting the human epidermis from UV rays, it is present in various forms which are usually used for this type. It can thus be, in particular, in the form of oily or oily-alcoholic lotions, emulsions, for instance as a cream or milk in the form of oily-alcoholic, oily-aqueous or aqueous-alcoholic gels, or as solid sticks, or can be made up as an aerosol.

It can comprise cosmetic adjuvants which are usually used in this type of agent, such as, for example, thickening agents, softening agents, moistening agents, surface-active agents, preservatives, agents which prevent foam formation, perfumes, waxes, lanolin, propellants, dyestuffs and/or pigments, which color the agent itself or the skin, and other ingredients usually used in cosmetics.

The compound of the formula I, preferably of the formula Ia, in particular wherein at least one of the radicals $R^1$ to $R^9$ is 2-ethylhexyloxy, is as a rule contained in an amount of 0.5 to 10%, preferably 1 to 8%, in particular 3 to 6%, based on the total weight of the cosmetic agent for protection of the human epidermis.

An oil, wax or other fatty substance, a lower monoalcohol or a lower polyol or mixtures thereof can be used as solubilizing agents. The particularly preferred monoalcohols or polyols include ethanol, i-propanol, propylene glycol, glycerol and sorbitol.

A preferred embodiment of the invention is an emulsion which is in the form of a protective cream or milk and comprises, in addition to the compound of the formula I, preferably of the formula Ia, in particular wherein at least one of the radicals $R^1$ to $R^9$ is 2-ethylhexyloxy, fatty alcohols, fatty acid esters, in particular triglycerides of fatty acids, fatty acids, lanolin, naturally occurring or synthetic oils or waxes and emulsifiers in the presence of water.

Other preferred embodiments are oily lotions based on naturally occurring or synthetic oils and waxes, lanolin, fatty acid esters, in particular triglycerides of fatty acids, or oily-alcoholic lotions based on a lower alcohol, such as ethanol, or on a glycol, such as propylene glycol, and/or on a polyol, such as glycerol, and oils, waxes and fatty acid esters, such as triglycerides of fatty acids.

The cosmetic agent according to the invention can also be in the form of an alcoholic gel which comprises one or more lower alcohols or polyols, such as ethanol, propylene glycol or glycerol, and a thickening agent, such as silica. The oily-alcoholic gels furthermore comprise naturally occurring or synthetic oil or wax.

The solid sticks comprise naturally occurring or synthetic waxes and oils, fatty alcohols, fatty acid esters, lanolin and other fatty substances.

The invention also relates to cosmetic sunscreen agents which comprise at least one compound of the formula I, preferably of the formula Ia, in particular wherein one of the radicals $R^1$ to $R^9$ is 2-ethylhexyloxy, and can comprise other UVB and/or UVA filters.

In this case, the amount of filter of the formula I is as a rule between 0.5 and 8.0% by weight, preferably 1 to 6% by weight, in particular 3 to 5% by weight, based on the total weight of the sunscreen agent.

If an agent is made up as an aerosol, the customary propellants, such as alkanes, fluoroalkanes and chlorofluoroalkanes, are used as a rule.

If the agent according to the invention is to protect natural or sensitized hair from UV rays, it can be in the form of a shampoo, lotion, gel or emulsion for rinsing out the particular formulation being applied before or after shampooing, before or after dyeing or bleaching or before or after a permanent wave. Alternatively, the agent is in the form of a lotion or gel for styling and treatment, in the form of a lotion or gel for brushing or setting a waterwave, or in the form of a hair lacquer, permanent wave agent or dyeing or bleaching agent for hair. In addition to the compound according to the invention, this agent can comprise various adjuvants used in this type of agent, such as surface-active agents, thickening agents, polymers, softening agents, preservatives, foam stabilizers, electrolytes, organic solvents, silicone derivatives, oils, waxes, antiseborrhoeic agents, dyestuffs and/or pigments which color the agent itself or the hair, or other ingredients usually used for hair care. The agent as a rule comprises 1.0 to 5.0% by weight of the compound of the formula I, preferably of the formula Ia, in particular wherein one of the radicals $R^1$ to $R^9$ is 2-ethylhexyloxy.

The present invention also relates to cosmetic agents which comprise at least one compound of the formula I, preferably of the formula Ia, in particular wherein one of the radicals $R^1$ to $R^9$ is 2-ethylhexyloxy, as agents for protection from UV rays and as antioxidizing agents; these agents include hair products, such as hair lacquers, waterwave lotions for setting the hair, if appropriate for treatment or easier styling, shampoos, coloring shampoos, hair coloring agents, make-up products, such as nail varnish, creams and oils for skin treatment, foundation, lipsticks, skin care agents, such as bath oils or creams, and other cosmetic agents which can cause problems with light stability and/or oxidation in the course of storage with respect to their components. Such agents as a rule comprise 1.0 to 5.0% by weight of a compound of the formula I, preferably of the formula Ia, in particular wherein one of the radicals $R^1$ to $R^9$ is 2-ethylhexyloxy.

The invention furthermore relates to a process for protection of cosmetic agents from UV rays, an active amount of at least one compound of the formula I, preferably of the formula Ia, in particular wherein one of the radicals $R^1$ to $R^9$ is 2-ethylhexyloxy, being added to these agents.

The invention furthermore relates to the use of the compounds of the formula I as sun filters having a wide absorption span in a wavelength range of 300 to 350 nm.

The compounds of the formula Ia, wherein at least one of the radicals $R^1$ to $R^9$ is 2-ethylhexyloxy, exhibit a significant pharmacological activity in the field of preventive treatment of inflammations and skin allergies.

The invention also relates to the compounds of the formula Ia, wherein at least one of the radicals $R^1$ to $R^9$ is 2-ethylhexyloxy, for use as a medicament.

The invention furthermore relates to a pharmaceutical agent which comprises an active amount of at least one compound of the formula Ia, wherein at least one of the radicals $R^1$ to $R^9$ is 2-ethylhexyloxy, as the active substance in a non-toxic carrier or excipient.

The pharmaceutical agent according to the invention can be administered orally or topically.

For oral administration, the pharmaceutical agent is present in the form of pastilles, gelatin capsules or coated tablets or as a syrup, suspension, solution, emulsion and the like. For topical application, it is present in the form of an ointment, cream, pomade, solution, lotion, gel, spray, suspension and the like.

This agent can comprise inert or pharmacodynamically active additives, in particular hydrating agents, antibiotics, steroid or non-steroid antiinflammatory agents, carotinoids and agents against psoriasis.

This agent can also comprise flavor-improving agents, preservatives, stabilizers, moisture regulators, pH regulators, modifiers for osmotic pressure, emulsifiers, local anesthetics, buffers and the like.

It can furthermore be conditioned in a manner which is known per se in a retarded form or in a form in which the active compound is released rapidly.

Even without further statements, it is assumed that an expert can utilize the above description in the broadest scope. The preferred embodiments are therefore to be interpreted merely as a descriptive disclosure and in no way as a disclosure which is limiting in any manner.

The complete disclosure of all the applications, patents and publications mentioned above and below and of the corresponding Application P 42 04 257, filed on Feb. 2, 1992, are incorporated in this Application by reference.

The following examples are intended to illustrate the invention.

PREPARATION EXAMPLES

The UV spectra were measured in a UV spectrometer from Perkin-Elmer at a path length of one centimeter.

EXAMPLE 1

2-[2',5'-Di(2-ethylhexyloxy)phenyl]benzimidazole 35 g (0.17 mol) of copper(II) acetate in 600 ml of water are added to a solution of 5.4 g (0.05 mol, of 1,2-phenylenediamine in 200 ml of methanol and the mixture is subsequently stirred briefly. 19 g (0.05 mol) of 2,5-di(2-ethylhexyloxy)benzaldehyde in 100 ml of methanol are then poured in and the mixture is heated under reflux. It is then filtered hot, ethanol is added, and $H_2S$ gas is passed through this suspension under reflux. The mixture is filtered hot with suction and the solution is concentrated. Purification is carried out by means of column chromatography. An oil is formed, the NMR, MS and IR spectra of which correspond to the expected structure.

UV (ethanol, c=1 mg/100 ml): $\lambda_{max1}$=303 nm, E=0.34 $\lambda_{max2}$=328 nm, E=0.30

The following are prepared analogously:

1.4-bis[5-n-Butylbenzimidazol-2-yl]benzene, melting point>300° C.

1.4-bis[5-i-butylbenzimidazol-2-yl]benzene, melting point>300° C.

1-(5-methylbenzimidazol-2-yl)-4-(5'-pentylbenzimidazol-2-yl)benzene, melting point>250° C.

2-(3'-hexyloxyphenyl)-benzimidazole, melting point=240°–241° C. (decomposition)

2-(4'-cyclohexyloxyphenyl)benzimidazole, melting point=265°–266° C.

2-(4'-(2-ethylhexyloxy)phenyl)benzimidazole, melting point=158°–159° C.

2-(3'-(2-ethylhexyloxy)phenyl)benzimidazole, melting point=140°–141° C.

2-(2'-(2-ethylhexyloxy)phenyl)benzimidazole, melting point=63°–65° C.

2-(3'-methoxy-4'-(2-ethylhexyloxy)phenyl)benzimidazole, oil 2-(4'-methoxy-3'-(2-ethylhexyloxy)phenyl)benzimidazole, oil 2-(2',5'-dimethoxyphenyl)-5-i-butylbenzimidazole, melting point=165°–166° C.

2-(2',5'-dimethoxyphenyl)-5-i-butylbenzimidazole, melting point=174°–175° C.

2-(2',5'-dimethoxyphenyl)-5-tert-butylbenzimidazole, melting point=212°–213° C.

2-(2',5'-dimethoxyphenyl)-5-n-pentylbenzimidazole, melting point=129°–131° C.

2-(2',5'-dimethoxyphenyl)-5-n-hexylbenzimidazole, Melting point=127°–128° C.

2-(2',5'-di(2-ethylhexyloxy)phenyl)-5-n-pentylbenzimidazole, oil.

Compounds of the formula Ia2

Ia2

| n | m | m.p. (°C.) |
|---|---|---|
| 4 | 4 | 102–103 |
| 5 | 5 | 89–90 |
| 6 | 6 | 72–73 |
| 7 | 7 | 66–67 |
| 8 | 8 | 70–72 |

2-[2',5'-Di(2-ethylhexyloxy)phenyl]-5-methylbenzimidazole, melting point –62° to –60° C. (oil)

Compounds of the formula Ia3

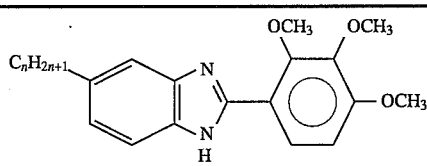

| n | melting point (°C.) |
|---|---|
| 4 (iso) | 85–86 |
| 4 (tert) | 125–127 |
| 5 (normal) | 86–87 |
| 6 (normal) | oil |

EXAMPLE 2

2-(2',4'-Dimethoxy-3'-(2-ethylhexyloxy)phenylbenzimidazole a) 2-(2',3',4'-Trimethoxy)phenylbenzimidazole 69 g (0.35 mol) of 2,3,4-trimethoxybenzaldehyde are added to 70 g (0.36 mol) of sodium disulfite in 800 ml of water and the mixture is subsequently stirred briefly. 35 g (0.32 mol) of phenylenediamine are added to this reaction mixture and the mixture is heated under reflux. The oil formed is separated off and recrystallized from toluene/petroleum ether. 62 g (68% of theory) of white crystals are formed. Melting point: 167° C.

UV (Ethanol, c=1 mg/100 ml): $\lambda_{max1}$309 nm, E=0.76 $\lambda_{max2}$=323 nm, E=0.42 b) 2-(2',4'-Dimethoxy-3'-hydroxy)phenylbenzimidazole 62 g (0.22 mol) of substance obtained according to the method 2a) are dissolved in 400 ml of a mixture of pyridine and collidine (1:1), and 88 g (0.66 mol) of lithium iodide are added in portions. The mixture is then boiled under reflux for 4 hours. When the reaction solution has been poured onto 600 ml of water, a neutral pH is established with concentrated HCl solution. The crystals which have precipitated out as a result are filtered off with suction, rinsed with water and dried. Yield: 44 g (75% of theory), melting point: 245° C.

c) 2-(2',4'-Dimethoxy-3'-(2-ethylhexyloxy)phenylbenzimidazole 47 g (0.34 mol) of potassium carbonate and 16 g (0.12 mol) of lithiumiodide are added to the 44 g (0.16 mol) of 2-(2',4'-dimethoxy-3'-hydroxy)phenylbenzimidazole obtained according to instructions b) in 400 ml of dimethylformamide. 50 g (0.34 mol) of 2-ethylhexyl chloride are added dropwise, while stirring, and the reaction solution is boiled under reflux. After the end of the reaction, the solution is poured onto water, and the organic phase is separated off and concentrated. Purification is carried out by means of column chromatography. 26 g of an oil (42% of theory) are formed. The spectra correspond to the expected compound.

UV (ethanol, c=1 mg/100 ml): $\lambda_{max1}$=297 nm, E=0.51 $\lambda_{max2}$=308 nm, 0.45

Solubility:
Paraffin: 5.7 g/100 ml
Miglyol: 59 g/100 ml
Isopropanol: 64 g/100 ml

USE EXAMPLES

In the following examples, the individual components are mixed with one another and homogenized as stated, if appropriate at elevated temperature. The mixture is then cooled, if appropriate while stirring, and, if desired, perfumed at 40° C.

EXAMPLE A

| Sunscreen cream (water-in-oil) | | | % |
|---|---|---|---|
| A | 2-[2',5'-Di(2-ethylhexyloxy)-phenyl]benzimidazole (from Example 1) | (1) | 4.00 |
| | Arlacel 581 | (2) | 6.00 |
| | Viscous paraffin (Art. No. 7160) | (1) | 17.50 |
| | Beeswax, bleached (Art. No. 11544) | (1) | 3.00 |
| | Miglyol 812 | (3) | 11.50 |
| | Dow Corning 200 (100 cs) | (4) | 2.00 |
| | Tocopherol acetate (Art. No. 500952) | (1) | 0.50 |
| B | Glycerol (Art.-No. 4093) | (1) | 2.00 |
| | Magnesium sulfate heptahydrate (Art. No. 5882) | (1) | 0.70 |
| | Preservative | | q.s. |
| | Water, demineralized | | to 100.00 |

Preparation:

Phase A is heated to 75° C. and phase B to 80° C. Phase B is stirred slowly into phase A.

Sources of supply:
(1) E. Merck, Darmstadt
(2) ICI, Essen
(3) Hüls Troisdorf Ag, Witten
(4) Dow Corning, Düsseldorf

EXAMPLE B

| Sunscreen cream (water-in-oil) | | | % |
|---|---|---|---|
| A | 2-[2',5'-Di(2-ethylhexyloxy)-phenyl]benzimidazole (from Example 1) | (1) | 6.00 |
| | Arlacel 581 | (2) | 6.00 |
| | Viscous paraffin (Art. No. 7160) | (1) | 17.50 |
| | Beeswax, bleached (Art. No. 11544) | (1) | 3.00 |
| | Miglyol 812 | (3) | 11.50 |
| | Dow Corning 200 (100 cs) | (4) | 2.00 |
| | Tocopherol acetate (Art. No. 500952) | (1) | 0.50 |
| B | Glycerol (Art.-No. 4093) | (1) | 2.00 |
| | Magnesium sulfate heptahydrate (Art. No. 5882) | (1) | 0.70 |
| | Preservative | | q.s. |
| | Water, demineralized | | to 100.00 |

Preparation:

Phase A is heated to 75° C. and phase B to 80° C. Phase B is stirred slowly into phase A.

Sources of supply:
(1) E. Merck, Darmstadt
(2) ICI, Essen
(3) Hüls Troisdorf Ag, Witten
(4) Dow Corning, Düsseldorf

EXAMPLE C

| Sunscreen gel (oil-containing) | | % |
|---|---|---|
| 2-[2',5'-Di(2-ethylhexyloxy)-phenyl]benzimidazole (from Example 1) | (1) | 5.00 |
| | (1) | 5.00 |
| Liquid paraffin (Art. No. 7162) | (1) | 20.00 |
| Miglyol 812 | (2) | 15.00 |
| Isopropyl myristate | (3) | 5.00 |
| Vaseline | (4) | 55.00 |

Preparation:

To dissolve, all the constituents are heated to 75° C.

Sources of supply:
(1) E. Merck, Darmstadt
(2) Hüls Troisdorf Ag, Witten
(3) Henkel, Düsseldorf
(4) E. Wagner, Bremen

EXAMPLE D

| Skin care cream (oil-in-water) | | | % |
|---|---|---|---|
| A | 2-[2',5'-Di(2-ethylhexyloxy)-phenyl]benzimidazole (from Example 1) | (1) | 4.00 |
| | Cutina KD 16 | (2) | 3.00 |
| | Stearic acid (Art. No. 671) | (1) | 2.00 |
| | Lanolin Corona | (3) | 3.00 |
| | Antaron V-220 | (4) | 1.00 |
| | Oxynex 2004 (Art. No. 6940) | (1) | 0.05 |
| B | Tris(hydroxymethyl)aminomethane (Art. No. 8386) | (1) | 0.81 |
| | Karion F liquid (Art. No. 2993) | (1) | 5.00 |
| | Carbopol 940 | (5) | 0.05 |
| | Preservative | | q.s. |
| | Water, demineralized | | to 100,00 |

Preparation:

Phase B is homogenized briefly. Phase A is heated to 75° C. and phase B to 80° C. Phase B is stirred slowly into phase A.

Sources of supply:
(1) E. Merck, Darmstadt
(2) Henkel, Düsseldorf
(3) Croda, Nettetal
(4) GAF, Frechen
(5) Goodrich, Neuss

EXAMPLE E

| Skin care cream (oil-in-water) | | | % |
|---|---|---|---|
| A | 2-[2',5'-Di(2-ethylhexyloxy)-phenyl]benzimidazole (from Example 1) | (1) | 6.00 |
| | Cutina KD 16 | (2) | 3.00 |
| | Stearic acid (Art. No. 671) | (1) | 2.00 |
| | Lanolin Corona | (3) | 3.00 |
| | Antaron V-220 | (4) | 1.00 |
| | Oxynex 2004 (Art. No. 6940) | (1) | 0.05 |
| B | Tris (hydroxymethyl)aminomethane (Art. No. 8386) | (1) | 0.81 |
| | Karion F liquid (Art. No. 2993) | (1) | 5.00 |
| | Carbopol 940 | (5) | 0.05 |
| | Preservative | | q.s. |
| | Water, demineralized | | to 100,00 |

Preparation:

Phase B is homogenized briefly. Phase A is heated to 75° C. and phase B to 80° C. Phase B is stirred slowly into phase A.

Sources of supply:
(1) E. Merck, Darmstadt
(2) Henkel, Düsseldorf
(3) Croda, Nettetal
(4) GAF, Frechen
(5) Goodrich, Neuss

EXAMPLE F

| Sunscren oil | | % |
|---|---|---|
| 2-[2',5'-Di(2-ethylhexyloxy)-phenyl]benzimidazole (from Example 1) | (1) | 5.00 |
| Highly liquid paraffin (Art. No. 7174) | (1) | 50.00 |
| Miglyol 812 | (2) | 15.00 |
| Cetiol B | (3) | 22.50 |
| Isopropyl myristate | (3) | 7.50 |

Preparation:

The mixture is heated at 70° C., while stirring, until all the components have dissolved.

Sources of supply:
(1) E. Merck, Darmstadt
(2) Hüls Troisdorf Ag, Witten
(3) Henkel, Düsseldorf

EXAMPLE G

| Sunscreen cream (water-in-oil) | | | % |
|---|---|---|---|
| A | 2-[2',4'-Dimethoxy-3'-(2-ethylhexyloxy)phenyl]benzimidazole (from Example 2) | (1) | 4.00 |
| | Arlacel 581 | (2) | 6.00 |
| | Viscous paraffin (Art. No. 7160) | (1) | 17.50 |
| | Beeswax, bleached (Art. No. 11544) | (1) | 3.00 |
| | Miglyol 812 | (3) | 11.50 |
| | Dow Corning 200 (100 cs) | (4) | 2.00 |
| | Tocopherol acetate (Art. No. 500952) | (1) | 0.50 |
| B | Glycerol (Art.-No. 4093) | (1) | 2.00 |
| | Magnesium sulfate heptahydrate (Art. No. 5882) | (1) | 0.70 |
| | Preservative | | q.s. |
| | Water, demineralized | | to 100.00 |

Preparation:

Phase A is heated to 75° C. and phase B to 80° C. Phase B is stirred slowly into phase A.

Sources of supply:
(1) E. Merck, Darmstadt
(2) ICI, Essen
(3) Hüls Troisdorf Ag, Witten
(4) Dow Corning, Düsseldorf

EXAMPLE H

| Sunscreen cream (water-in-oil) | | | % |
|---|---|---|---|
| A | 2-[2',4'-Dimethoxy-3'-(2-ethylhexyloxy)phenyl]benzimidazole (from Example 2 | (1) | 6.00 |
| | Arlacel 581 | (2) | 6.00 |
| | Viscous paraffin (Art. No. 7160) | (1) | 17.50 |
| | Beeswax, bleached (Art. No. 11544) | (1) | 3.00 |
| | Miglyol 812 | (3) | 11.50 |
| | Dow Corning 200 (100 cs) | (4) | 2.00 |
| | Tocopherol acetate (Art. No. 500952) | (1) | 0.50 |
| B | Glycerol (Art.-No. 4093) | (1) | 2.00 |
| | Magnesium sulfate heptahydrate (Art. No. 5882) | (1) | 0.70 |
| | Preservative | | q.s. |
| | Water, demineralized | | to 100.00 |

Preparation:

Phase A is heated to 75° C. and phase B to 80° C. Phase B is stirred slowly into phase A.

Sources of supply:
(1) E. Merck, Darmstadt
(2) ICI, Essen
(3) Hüls Troisdorf Ag, Witten
(4) Dow Corning, Düsseldorf

EXAMPLE I

| Sunscreen oil | | % |
|---|---|---|
| 2-[2',4'-Dimethoxy-3'-(2-ethylhexyloxy)phenyl]benzimidazole (from Example 2) | (1) | 5.00 |
| Highly liquid paraffin (Art. No. 7174) | (1) | 50.00 |
| Miglyol 812 | (2) | 15.00 |
| Cetiol B | (3) | 22.50 |
| Isopropyl myristate | (3) | 7.50 |

Preparation:

The mixture is heated at 70° C., while stirring, until all the components have dissolved.

Sources of supply:
(1) E. Merck, Darmstadt
(2) Hüls Troisdorf Ag, Witten
(3) Henkel, Düsseldorf

EXAMPLE J

| Skin care cream (oil-in-water) with lanolin | | | % |
|---|---|---|---|
| A | 2-[2',4'-Dimethoxy-3'-(2-ethylhexyloxy)phenyl]benzimidazole (from Example 2) | (1) | 4.00 |
| | Cutina KD 16 | (2) | 3.00 |
| | Stearic acid (Art. No. 671) | (1) | 2.00 |
| | Lanolin Corona | (3) | 3.00 |
| | Antaron V-220 | (4) | 1.00 |
| | Oxynex 2004 (Art. No. 6940) | (1) | 0.05 |
| B | Tris(hydroxymethyl)aminomethane (Art. No. 8386) | (1) | 0.81 |
| | Karion F liquid (Art. No. 2993) | (1) | 5.00 |
| | Carbopol 940 | (5) | 0.05 |
| | Preservative | | q.s. |
| | Water, demineralized | | to 100,00 |

Preparation:

Phase B is homogenized briefly. Phase A is heated to 75° C. and phase B to 80° C. Phase B is stirred slowly into phase A.

Sources of supply:
(1) E. Merck, Darmstadt
(2) Henkel, Düsseldorf
(3) Croda, Nettetal
(4) GAF, Frechen
(5) Goodrich, Neuss

EXAMPLE K

| Skin care cream (oil-in-water) with lanolin | | | % |
|---|---|---|---|
| A | 2-[2',4'-Dimethoxy-3'-(2-ethylhexyloxy)phenyl]benzimidazole (from | (1) | 6.00 |

13
-continued

| Skin care cream (oil-in-water) with lanolin | | % |
|---|---|---|
| Example 2) | (2) | 3.00 |
| Cutina KD 16 | (2) | 3.00 |
| Stearic acid (Art. No. 671) | (1) | 2.00 |
| Lanolin Corona | (3) | 3.00 |
| Antaron V-220 | (4) | 1.00 |
| Oxynex 2004 (Art. No. 6940) | (1) | 0.05 |
| B  Tris(hydroxymethyl)aminomethane (Art. No. 8386) | (1) | 0.81 |
| Karion F liquid (Art. No. 2993) | (1) | 5.00 |
| Carbopol 940 | (5) | 0.05 |
| Preservative | | q.s. |
| Water, demineralized | | to 100,00 |

Preparation:

Phase B is homogenized briefly. Phase A is heated to 75° C. and phase B to 80° C. Phase B is stirred slowly into phase A.

Sources of supply:
(1) E. Merck, Darmstadt
(2) Henkel, Düsseldorf
(3) Croda, Nettetal
(4) GAF, Frechen
(5) Goodrich, Neuss

EXAMPLE L

| Sunscreen gel (oil- containing) | | % |
|---|---|---|
| 2-[2',4'-Dimethoxy-3'-(2-ethylhexyloxy) phenyl]benzimidazole (from Example 2) | (1) | 5.00 |
| Liquid paraffin (Art. No. 7162) | (1) | 20.00 |
| Miglyol 812 | (2) | 15.00 |
| Isopropyl myristate | (3) | 5.00 |
| Vaseline | (4) | 55.00 |

Preparation:
To dissolve, all the constituents are heated to 75° C.

Sources of supply:
(1) E. Merck, Darmstadt
(2) Hüls Troisdorf Ag, Witten
(3) Henkel, Düsseldorf
(4) E. Wagner, Bremen

We claim:

1. A cosmetic composition comprising, as light protection filters, at least one benzimidazole of the formula

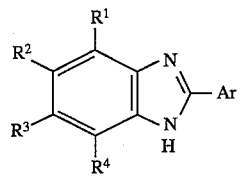

in which $R^1$, $R^2$, $R^3$ and $R^4$ in each case independently of one another are H, alkyl or alkoxy having 1 to 10 C atoms and Ar is phenyl which is unsubstituted or substituted by 1–5 aminoalkyl, alkyl, alkoxy, cycloalkoxy, hydroxyl or hydroxyalkoxy groups having 1 to 10 C atoms or benzimidazole-2-yl-phenyl which is monosubstituted with 1 to 2 alkyl groups having 1 to 10 C atoms, wherein at least one of the radicals $R^1$ to $R^4$ or an alkoxy substituent on the group Ar is a 2-ethylhexyloxy group.

2. A cosmetic composition according to claim 1, comprising at least one benzimidazole of the formula Ia:

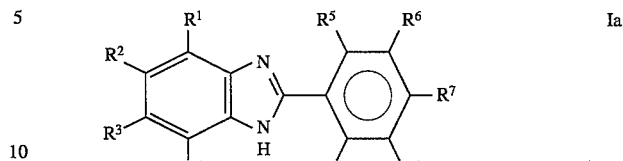

wherein at least one of the groups $R^1$ to $R^8$ is a 2-ethylhexyloxy group and the other groups $R^1$ to $R^9$ are H, alkyl or alkoxy having 1 to 10 C atoms.

3. A benzimidazole of the formula Ia,

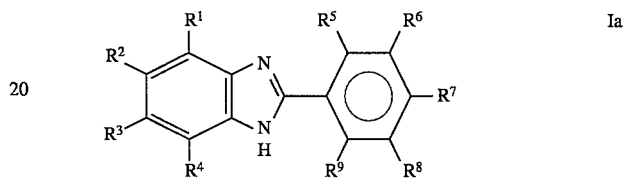

wherein at least one of the groups $R^1$ to $R^9$ is a 2-ethylhexyloxy group and the other groups $R^1$ to $R^9$ are H, alkyl or alkoxy having 1 to 10 C atoms.

4. A cosmetic composition according to claim 1 further comprising a cosmetically compatible carrier.

5. A cosmetic composition according to claim 4, where the carrier has at least one fat phase.

6. A cosmetic composition according to claim 4, characterized in that it comprises 0.5 to 10% by weight of at least one compound of the formula I.

7. A cosmetic composition according to claim 4, characterized in that it additionally comprises a UV-B filter.

8. A cosmetic composition according to claim 4, which comprises at least one compound of the formula Ia:

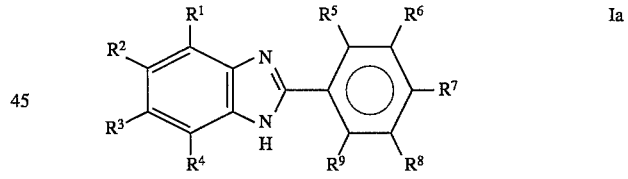

wherein at least one of the groups $R^1$ to $R^9$ is a 2-ethylhexyloxy group and the other groups $R^1$ to $R^9$ are H, alkyl or alkoxy having 1 to 10 C atoms.

9. A cosmetic composition according to claim 1, which comprises at least one compound of the formula Ia1:

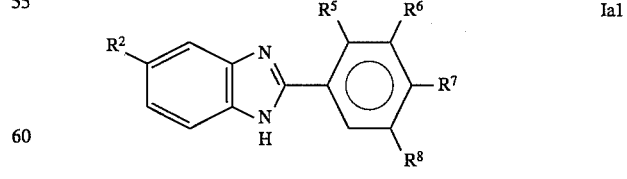

wherein $R^2$ is H or alkyl having 1 to 6 C atoms, one or two of the radicals $R^5$ to $R^8$ are a 2-ethylhexyloxy group and the other radicals $R^5$ to $R^8$ are H or methoxy.

10. A cosmetic composition according to claim 1, which comprises at least one compound of the formula Ia2:

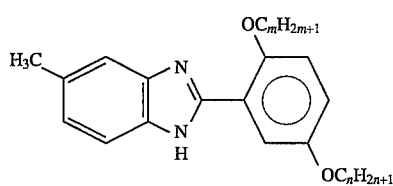
wherein m and n are in each case independently of one another an integer of 4 to 10, provided that at least one of $C_mH_{2m+1}$ or $C_nH_{2n+1}$ is a 2-ethylhexyl group.
11. A cosmetic composition according to claim 1, which comprises 1 to 8%, based on the total weight of the composition, of at least one compound of the formula I.
* * * * *